an asco-
United States Patent [19]
Yaver et al.

[11] Patent Number: 5,688,663
[45] Date of Patent: Nov. 18, 1997

[54] **GENE ENCODING CARBOXYPEPTIDASE OF *ASPERGILLUS NIGER***

[75] Inventors: Debbie Sue Yaver; Sheryl Ann Thompson, both of Davis, Calif.

[73] Assignee: Novo Nordisk Biotech, Inc., Davis, Calif.

[21] Appl. No.: 608,267

[22] Filed: Feb. 28, 1996

Related U.S. Application Data

[62] Division of Ser. No. 309,341, Sep. 20, 1994, Pat. No. 5,594,119.

[51] Int. Cl.$^6$ .............. C12P 21/06; C12N 15/00; C12N 1/14; C12N 1/16
[52] U.S. Cl. .............. 435/69.1; 435/172.3; 435/254.11; 435/254.3
[58] Field of Search .............. 435/69.1, 172.3, 435/254.11, 254.3

[56] References Cited

FOREIGN PATENT DOCUMENTS

WO 92/17595  10/1992  WIPO .

OTHER PUBLICATIONS

Dal Degan et al. (1992) Appl. and Environ. Microbiol. 58(7): 2144–2152.
de Ruiter–Jacobs et al. (1989) Curr. Genetics 16: 159–163.
Krishnan et al. (1986) J. Chromatog. 370: 315–326.
Sørensen et al., Carlsberg Res. Commun., vol. 54, pp. 193–202 (1989).
Jarai et al., Gene, vol. 145, pp. 171–178 (1994).
Frederick et al., Gene, vol. 125, pp. 57–64 (1993).
Svendsen et al., FEBS Letters, vol. 333, No. 1,2, pp. 39–43 (1993).
Woolford et al., Molecular & Cellular Biology, vol. 6, No. 7, pp. 2500–2510 (1986).
Mukhtar et al., Gene, vol. 121, pp. 173–177 (1992).
Ammerer et al., Molecular & Cellular Biology, vol. 6, No. 7, pp. 2490–2499 (1986).
Stevens et al., J. of Cell Biology, vol. 102, pp. 1551–1557 (1986).
Rodney Rothstein, Methods in Enzymology, vol. 194, pp. 281–301 (1991).
L. Valls et al., Cell, vol. 48, pp. 887–897 (1987).
Berka et al., Gene, vol. 86, No. 2, pp. 153–162 (1990).
Yaver et al., 34th Annual Meeting of ASCB, Molecular Biol. Cell, 5 (Suppl.) ISSN: 1059–1525 (1994).

*Primary Examiner*—Robert A. Wax
*Assistant Examiner*—Lisa J. Hobbs
*Attorney, Agent, or Firm*—Steve T. Zelson, Esq.; Elias J. Lambiris, Esq.

[57] ABSTRACT

The present invention relates to a gene encoding an ascomycete or deuteromycete carboxypeptidase Y gene, and host cells modified so as to produce reduced amounts of carboxypeptidase.

22 Claims, 13 Drawing Sheets

FIG. 1
(1 OF 6)

```
                                                                                    60
TCCTCTGCCT ACTCATCCCA TCACCATCTC AATTCATACC GCCCCCGTGG GGTTTCAGCA CCA 69          78          87          96         105         114
 >
 ATG AGA GTC CTT GCT GCT ATG CTG GTT GGA GCG GCC ACG GCG GCC GTT CCT
 MET Arg Val Leu Pro Ala Ala MET Leu Val Gly Ala Ala Thr Ala Ala Val Pro 123         132         141         150         159         168
 CCC TTC CAG CAG GTC CTT GGA GGT AAC GGT GCC AAG CAC GGT GCC GAC CAT GCG
 Pro Phe Gln Gln Val Leu Gly Gly Asn Gly Ala Lys His Gly Ala Asp His Ala 177         186         195         204         213         222
 GCC GAG GTC CCT GCG GAT CAC AGT GCC GAC GGG TTC TCC AAG CCG CTG CAC GCA
 Ala Glu Val Pro Ala Asp His Ser Ala Asp Gly Phe Ser Lys Pro Leu His Ala 231         240         249         258         267         276
 TTC CAG GAG GAG CTG AAG TCT CTC TCT GAC GAG GCT CGT AAG CTT TGG GAT GAG
 Phe Gln Glu Glu Leu Lys Ser Leu Ser Asp Glu Ala Arg Lys Leu Trp Asp Glu 285         294         303         312         321         330
 GCC AGC TTC TTC CCG GAG AGC ATG GAT CAG AAC CCT CTC TTT TCC CTC CCC
 Ala Ser Phe Phe Pro Glu Ser MET Asp Gln Asn Pro Leu Phe Ser Leu Pro

GTG GCC
 Val Ala
```

FIG. 1
(2 OF 6)

```
     339        348        357        366        375        384
     |          |          |          |          |          |
AAG  AAC  CAC  CGT  CCC  GAC  TCG  CAC  TGG  GAC  CAC  ATC  GTC  CGC  GGC  TCC
Lys  Asn  His  Arg  Pro  Asp  Ser  His  Trp  Asp  His  Ile  Val  Arg  Gly  Ser 393        402        411        420        429        438
     |          |          |          |          |          |
GAC  GTT  CAG  AGC  GTC  TGG  GTC  ACT  GGT  GAG  AAC  GGT  GAG  AAG  GAG  CGC  GAG  GTC
Asp  Val  Gln  Ser  Val  Trp  Val  Thr  Gly  Glu  Asn  Gly  Glu  Lys  Glu  Arg  Glu  Val 447        456        465        474        483        492
     |          |          |          |          |          |
GAT  AAG  CTG  GAA  GCC  TAT  GAT  CTC  AGG  GTC  AAG  AAG  ACC  GAT  CCT  GGC  TCT
Asp  Lys  Leu  Glu  Ala  Tyr  Asp  Leu  Arg  Val  Lys  Lys  Thr  Asp  Pro  Gly  Ser 501        510        519        528        537        546
     |          |          |          |          |          |
CTT  GGC  ATC  GAC  CCC  GGC  GTG  CAG  TAC  ACC  GGT  TAT  CTC  GAT  GAC  AAC  GAG
Leu  Gly  Ile  Asp  Pro  Gly  Val  Lys  Gln  Tyr  Thr  Gly  Tyr  Leu  Asp  Asp  Asn  Glu 555        564                                               581         591        601        611
     |          |                                                 |           |          |          |
AAT  GAT  AAG  CAT  TTG  TTC  TAC  T     GTAAGCACAC  CTTGGTTCAA  GATCACGCTT  TTTATATGCT
Asn  Asp  Lys  His  Leu  Phe  Tyr  Trp

CTGGATATCT  AACGCAACTT  AG  GG  TTC  TTC  GAG  TCT  CGC  AAT  GAC  CCC  GAG  AAT  GAT
                              Phe  Phe  Glu  Ser  Arg  Asn  Asp  Pro  Glu  Asn  Asp
            621                631             641        650        659        668
```

FIG. 1
(3 OF 6)

```
     677              686              695              704              713              722
      |  CCC GTT CTG | TGG AAC GGT  | CCT GGC TGC  | TCC TCT CTC  | ACC GGT CTC |
         Pro Val Val   Leu Trp Asn    Gly Pro Gly    Cys Ser Ser    Leu Thr Gly  Leu 731              740              749              758              767              776
      |  TTC ATG GAG | CTT GGC CCT  | AGC AGC ATC  | AAC AAG AAG  | ATC CAG CCG |
         Phe MET Glu   Leu Gly Pro    Ser Ser Ile    Asn Lys Lys    Ile Gln Pro  Val Tyr Asn 785              794              803              812              821              830
      |  GAC TAC GCT | TGG AAC TCC  | AAC GCG TCC  | GTG ATC TTC  | CTT GAC CAG |
         Asp Tyr Ala   Trp Asn Ser    Asn Ala Ser    Val Ile Phe    Leu Asp Gln  Pro Val Asn 839              848              857              866              875              884
      |  GTC GGT TAC | TCC TAC AGT  | AAC TCT GCT  | GTC AGC GAC  | ACG GTC GCT |
         Val Gly Tyr   Ser Tyr Ser    Asn Ser Ala    Val Ser Asp    Thr Val Ala  Gly Lys 893              902              911              920              929              938
      |  TAT GCC TTG | ACC CTC TTC  | TTC TCT GCT  | GAC CAA TTC  | CCC GAG TAT |
         Tyr Ala Leu   Thr Leu Phe    Phe Ser Ala    Asp Gln Phe    Pro Glu Tyr  Ala Lys 947              956              965              974              983              992
      |  TAT GCC GGT | GAA TCT TAT  | GCT GGT CAC  | TAT GCT CAC  | TAT ATC CCC |
         Tyr Ala Gly   Glu Ser Tyr    Ala Gly His    Tyr Ala His    Tyr Ile Pro  Val Phe

|  CAG GAC TTC | CAC ATT GCC  | GGT GAA TCT  | TAT GCT GGT  | CAC TAT GCT |
         Gln Asp Phe   His Ile Ala    Gly Glu Ser    Tyr Ala Gly    His Tyr Ala
```

FIG. I
(4 OF 6)

```
      1001        1010        1019        1028        1037        1046
      |           |           |           |           |           |
      GCT TCG GAG ATC CTG TCT CAC AAG AAG CGC AAC ATC AAC CTG CAG TCC GTT CTC
      Ala Ser Glu Ile Leu Ser His Lys Lys Arg Asn Ile Asn Leu Gln Ser Val Leu 1055        1064        1073        1082        1091        1100
      |           |           |           |           |           |
      ATT GGC AAC GGT CTC ACC GAC GGA TAC ACC CAG TAC GAG TAC TAC CGT CCC ATG
      Ile Gly Asn Gly Leu Thr Asp Gly Tyr Thr Gln Tyr Glu Tyr Tyr Arg Pro MET 1109        1118        1127        1136        1145        1154
      |           |           |           |           |           |
      GCC TGC GGT GAC GGC GGT TAC CCA GCT GTC TTG GAC GAG AGC TCC TGC CAG TCC
      Ala Cys Gly Asp Gly Gly Tyr Pro Ala Val Leu Asp Glu Ser Ser Cys Gln Ser 1163        1172        1181        1190        1199        1208
      |           |           |           |           |           |
      ATG GAC AAC GCT CTT CCT CGC TGC CAG TCT ATG ATT GAG TCT TGC TAC AGT TCC
      MET Asp Asn Ala Leu Pro Arg Cys Gln Ser MET Ile Glu Ser Cys Tyr Ser Ser 1217        1226        1235        1244        1253        1262
      |           |           |           |           |           |
      GAG AGC GCT TGG GTT TGT GTC CCG GCC TCC ATC TAC TGT AAC AAC GCC CTC CTT
      Glu Ser Ala Trp Val Cys Val Pro Ala Ser Ile Tyr Cys Asn Asn Ala Leu Leu 1271        1280        1289        1298        1307        1316
      |           |           |           |           |           |
      GCC CCT TAC CAG CGC ACT GGG CAG AAC GTC TAT GAT GTC CGT GGT AAG TGC GAG
      Ala Pro Tyr Gln Arg Thr Gly Gln Asn Val Tyr Asp Val Arg Gly Lys Cys Glu
```

FIG. 1
(5 OF 6)

```
     1325      1334      1343      1352      1361      1370
      |         |         |         |         |         |
GAT  AGC TCT  AAC CTT  TGC TAC  TCG GCT  ATG GGC  TAC GTC  AGC GAC  TAC CTG  AAC
Asp  Ser Ser  Asn Leu  Cys Tyr  Ser Ala  MET Gly  Tyr Val  Ser Asp  Tyr Leu  Asn 1379      1388      1397      1406      1415      1424
      |         |         |         |         |         |
AAG  CCC GAA  GTC ATC  GAG GCT  GTT GGC  GCT GAG  GTC AAC  GGC TAC  GAC TCG  TGC
Lys  Pro Glu  Val Ile  Glu Ala  Val Gly  Ala Glu  Val Asn  Gly Tyr  Asp Ser  Cys 1433      1442      1451      1460      1469      1478
      |         |         |         |         |         |
AAC  TTT GAC  ATC AAC  CGC AAC  TTC CTC  TTC CAC  GGT GAC  TGG ATG  AAG CCC  TAC
Asn  Phe Asp  Ile Asn  Arg Asn  Phe Leu  Phe His  Gly Asp  Trp MET  Lys Pro  Tyr 1487      1496      1505      1514      1523      1532
      |         |         |         |         |         |
CAC  CGC CTC  GTT CCG  GGA CTC  CTG GAG  CAG ATC  CCT GTC  TTG ATC  TAT GCC  GGT
His  Arg Leu  Val Pro  Gly Leu  Leu Glu  Gln Ile  Pro Val  Leu Ile  Tyr Ala  Gly 1541      1550      1559      1568      1577      1586
      |         |         |         |         |         |
GAT  GCT GAT  TTC ATT  TGC AAC  TGG CTG  GGC AAC  AAG GCC  TGG ACT  GAA GCC  CTG
Asp  Ala Asp  Phe Ile  Cys Asn  Trp Leu  Gly Asn  Lys Ala  Trp Thr  Glu Ala  Leu 1595      1604      1613      1622      1631      1640
      |         |         |         |         |         |
GAG  TGG CCC  GGA CAG  GCT GAA  TAT GCC  TCC GCT  GAG CTG  GAG GAT  CTG GTC  ATT
Glu  Trp Pro  Gly Gln  Ala Glu  Tyr Ala  Ser Ala  Glu Leu  Glu Asp  Leu Val  Ile
```

FIG. 1 (6 OF 6)

```
     1649        1658        1667        1676        1685        1694
     GTC GAC AAT GAG CAC ACG GGC AAG AAG ATT GGC CAG GTT AAG TCC CAT GGC AAC
     Val Asp Asn Glu His Thr Gly Lys Lys Ile Gly Gln Val Lys Ser His Gly Asn 1703        1712        1721        1730        1739        1748
     TTC ACC TTC ATG CGT CTC TAT GGT GGT GGC CAC ATG GTC CCG ATG GAC CAG CCC
     Phe Thr Phe MET Arg Leu Tyr Gly Gly Gly His MET Val Pro MET Asp Gln Pro 1757        1766        1775        1784        1793                1809
     GAG TCG AGT CTC GAG TTC TTC AAC CGC TGG TTG GGA GGT GAA TGG TTC TAA AGACGTGCTA
     Glu Ser Ser Leu Glu Phe Phe Asn Arg Trp Leu Gly Gly Glu Trp Phe 1819        1829        1839        1849        1859        1869        1879
     CCACCGCATA TAGACTTTCT GGTCATTTCG GTGACACTGC AGATATAGTTT CTTAACGATA GTTTGAGCAT 1889        1899        1909        1919        1929        1939        1949
     GCTTGTCAAT GCCCACTAGT CCCGATCCTT ATATGTTGCA TGGTATCTAT GAGTTTTGTC ACTATAGTGC 1959        1969        1979        1989        1999        2009        2019
     ATTATACATG TGTACTTCGT ATGAGAATGA ATCGATCGCA TTTACACGCA TATAAATAGT ACCCACCTCC 2029        2039        2049        2059        2068
     GCCTGGACAT GAATTAGGCC CGGCCAGTCG TTTACATACA GTGCTAGAA
```

FIG. 2
(1 OF 6)

```
                 10         20         30         40         50         60         70
             GCGGCCGCTG CTACTTGCTT TTTCTAATTT GATACTTTG TGTCCGTACC GTACCTTCCA GACCGCAAGG
                 80         90        100        110        120        130        139
             TACCCATCCT CTACCTACTC ATCCCATCAT CATCTCGATT TCATACCAAC CCGTTGGGT TTCAACACA start of propeptide
                                                                          1 ↓  193
       148         157         166         175                          238            247
>  ATG AGA GTT CTT CCA GCT GCT ATG CTG GTT GGA GCG GGC ACT GCG GCC GTC CCT
   MET Arg Val Leu Pro Ala Ala MET Leu Val Gly Ala Gly Thr Ala Ala Val Pro 202         211         220         229
   CCC TTC CAG CAG GTC CTT GGT GGA AAC GGT GCC AAG CAC GGT GCC GAC CAT GCG
   Pro Phe Gln Gln Val Leu Gly Gly Asn Gly Ala Lys His Gly Ala Asp His Ala 256         265         274         283                          292            301
   GCC GAG GTC CCT GCG GAT CAC AGT GCC GAC GGG TTC TCC AAG CCG CTG CAC GCA
   Ala Glu Val Pro Ala Asp His Ser Ala Asp Gly Phe Ser Lys Pro Leu His Ala 310         319         328         337                          346            355
   GAG GAG CTG AAG TCT CTC GAT GAG GCT CGT AAG CTC TGG GAT GAG
   Glu Glu Leu Lys Ser Leu Asp Glu Ala Arg Lys Leu Trp Asp Glu TTC CAG GAG GAG CTG AAG TCT CTC GAT GAG GCT CGT AAG CTC TGG GAT GAG
   Phe Gln Glu Glu Leu Lys Ser Leu Asp Glu Ala Arg Lys Leu Trp Asp Glu
```

FIG. 2
(2 OF 6)

```
      364         373         382         391         400         409
      |           |           |           |           |           |
GTT   GCT   AGC   TTC   TTC   GAG   AGC   ATG   GAT   CAG   AAC   CCT   CTC   TTC   TCC   CTC   CCC
Val   Ala   Ser   Phe   Phe   Glu   Ser   MET   Asp   Gln   Asn   Pro   Leu   Phe   Ser   Leu   Pro 418         427         436         445         454         463
      |           |           |           |           |           |
AAG   AAC   CGC   CGC   CCC   GAC   CAC   TGG   CAC   ATC   GTC   CGC   GGC   TCC
Lys   Asn   Arg   Arg   Pro   Asp   His   Trp   His   Ile   Val   Arg   Gly   Ser 472         481         490         499         508         517
      |           |           |           |           |           |
GAC   GTT   CAG   AGC   GTC   TGG   GTT   ACT   GGT   GAG   AAC   GGT   GAG   AAG   GAG   CGT   GAG   GTC
Asp   Val   Gln   Ser   Val   Trp   Val   Thr   Gly   Glu   Asn   Gly   Glu   Lys   Glu   Arg   Glu   Val
                                                      predicted N-terminus of mature CPY
                                                      553 ↓

526         535         544         562         571
      |           |           |           |           |
GAT   GGC   AAG   CTG   GAA   GCC   TAT   GAT   CTC   AGG   GTC   AAG   AAG   ACC   GAT   CCT   AGC   TCT
Asp   Gly   Lys   Leu   Glu   Ala   Tyr   Asp   Leu   Arg   Val   Lys   Lys   Thr   Asp   Pro   Ser   Ser 580         589         598         607         616         625
      |           |           |           |           |           |
CTT   GGC   ATC   GAC   CCT   GGC   GTA   AAG   CAG   TAC   ACC   GGT   TAT   CTC   GAT   GAC   AAC   GAG
Leu   Gly   Ile   Asp   Pro   Gly   Val   Lys   Gln   Tyr   Thr   Gly   Tyr   Leu   Asp   Asp   Asn   Glu
```

FIG.2
(3 OF 6)

```
         634                643           652           661           670           679
    AAC  GAC  AAG  CAT  CTG  TTC  TAC  TGG  TTC  GAG  TCT  CGC  AAT  GAC  CCC  GAG  AAT
    Asn  Asp  Lys  His  Leu Phe  Tyr  Trp  Phe  Glu  Ser  Arg  Asn  Asp  Pro  Glu  Asn
         688                697           706           715           724           733
    GAC  CCT  GTT  GTT  CTG  TGG  CTG  AAC  GGT  CCT  GGA  TGC  TCC  TCC  CTC  ACC  GGT
    Asp  Pro  Val  Val  Leu  Trp  Leu  Asn  Gly  Pro  Gly  Cys  Ser  Ser  Leu  Thr  Gly
         742                751           760           769           778           787
    CTT  TTC  ATG  GAG  CTC  GGC  CCT  AGC  AGC  GGA  CCT  TCT  TCC  CTC  ACC  GTC  TAC
    Leu  Phe  MET  Glu  Leu  Gly  Pro  Ser  Ser  Gly  Pro  Ser  Ser  Leu  Thr  Val  Tyr
         796                805           814           823           832           841
    AAC  GAC  TAC  TGG  AAC  TCC  AAC  GCG  TCC  GTG  ATC  AAG  AAG  ATC  CAG  CCG  GTC
    Asn  Asp  Tyr  Trp  Asn  Ser  Asn  Ala  Ser  Val  Ile  Lys  Lys  Ile  Gln  Pro  Val
         850                859           868           877           886           895
    TAC  GCT  TCT  TAC  AGC  AAC  GCT  GTC  AGC  ATC  TTC  CTT  GAC  CAG  CCT  GCT  GGC
    Tyr  Ala  Ser  Tyr  Ser  Asn  Ala  Val  Ser  Ile  Phe  Leu  Asp  Gln  Pro  Ala  Gly
         904                913           922           931           940           949
    GTC  TAT  GCC  TTG  CTT  CTC  TTC  ACC  AGC  GAC  ACC  CCC  GAG  TAT  GGC
    Val  Tyr  Ala  Leu  Leu  Leu  Phe  Thr  Ser  Asp  Thr  Pro  Glu  Tyr  Gly
    AAG  GTC  TAT  GCC  CTC  TTG  CTT  CTC  TTC  AAA  CAA  TTC  CCC  GAG  TAT  GCC
    Lys  Val  Tyr  Ala  Leu  Leu  Leu  Phe  Lys  Gln  Phe  Pro  Glu  Tyr  Ala
```

FIG. 2
(4 OF 6)

```
 958         967         976         985         994        1003
  |           |           |           |           |           |
AAG CAG GAC TTC CAC ATT GCC GGT TCC TAT GCT GGT CAC TAT ATC CCC GTC
Lys Gln Asp Phe His Ile Ala Gly Ser Tyr Ala Gly His Tyr Ile Pro Val 1012        1021        1030        1039        1048        1057
  |           |           |           |           |           |
TTT GCT TCG GAG ATT TTG TCT CAC AAG AAG CGC AAC ATC AAC CTG CAG TCC GTT
Phe Ala Ser Glu Ile Leu Ser His Lys Lys Arg Asn Ile Asn Leu Gln Ser Val 1066        1075        1084        1093        1102        1111
  |           |           |           |           |           |
CTT ATT GGC AAC GGT CTC ACC GAC GGT CTC ACT CAG TAC CAG TAC TAC CGT CCC
Leu Ile Gly Asn Gly Leu Thr Asp Gly Leu Thr Gln Tyr Gln Tyr Tyr Arg Pro 1120        1129        1138        1147        1156        1165
  |           |           |           |           |           |
ATG GCC TGT GGT GAC GGT TAC CCA GCT GTC TTG GAC GAG GGC TCC TGC CAG
MET Ala Cys Gly Asp Gly Tyr Pro Ala Val Leu Asp Glu Gly Ser Cys Gln 1174        1183        1192        1201        1210        1219
  |           |           |           |           |           |
GCC GAC AAC GCC CTT CCT CGC TGC CAG TCT ATG ATT GAG TCT TGC TAT AGT
Ala Asp Asn Ala Leu Pro Arg Cys Gln Ser MET Ile Glu Ser Cys Tyr Ser 1228        1237        1246        1255        1264        1273
  |           |           |           |           |           |
GCC ATG GCT TGG GTT GTC TGT CCG GCC TCC ATC TAC TGT AAC AAC GCC CTC
Ala MET Ala Trp Val Cys Val Pro Ala Ser Ile Tyr Cys Asn Asn Ala Leu

|
TCC GAG AGC GCT
Ser Glu Ser Ala
```

FIG. 2
(5 OF 6)

```
      1282        1291        1300        1309        1318        1327
CTT | GCC | CCT | TAC | CAG | CGC | ACC | GGA | CAG | AAC | GTC | TAC | GAT | GTT | CGT | GGT | AAG | TGC
Leu   Ala   Pro   Tyr   Gln   Arg   Thr   Gly   Gln   Asn   Val   Tyr   Asp   Val   Arg   Gly   Lys   Cys 1336        1345        1354        1363        1372        1381
GAG | GAT | AGC | TCC | AAC | CTC | TGC | TAC | TCG | GCC | ATG | GGC | TAC | GTC | AGC | GAC | TAC | CTG
Glu   Asp   Ser   Ser   Asn   Leu   Cys   Tyr   Ser   Ala   MET   Gly   Tyr   Val   Ser   Asp   Tyr   Leu 1390        1399        1408        1417        1426        1435
AAC | AAG | ACC | GAG | ATT | GAG | GCT | GTT | GGC | GCT | GAG | GTC | AAC | GGC | TAC | GAC | TCG
Asn   Lys   Thr   Glu   Ile   Glu   Ala   Val   Gly   Ala   Glu   Val   Asn   Gly   Tyr   Asp   Ser 1444        1453        1462        1471        1480        1489
TGC | AAC | TTT | GAC | ATC | AAC | CGC | AAC | TTC | CTC | TTC | CAC | GGT | GAC | TGG | ATG | AAG | CCC
Cys   Asn   Phe   Asp   Ile   Asn   Arg   Asn   Phe   Leu   Phe   His   Gly   Asp   Trp   MET   Lys   Pro 1498        1507        1516        1525        1534        1543
TAC | CAC | CGT | CTC | GTT | CCG | GGA | CTC | CTG | GAG | CAG | ATC | CCT | GTC | CTG | ATC | TAC | GCT
Tyr   His   Arg   Leu   Val   Pro   Gly   Leu   Leu   Glu   Gln   Ile   Pro   Val   Leu   Ile   Tyr   Ala 1552        1561        1570        1579        1588        1597
TAC | CAC | GAT | TTC | ATC | TGC | AAC | TGG | CTG | GGC | AAC | AAG | GCC | TGG | ACT | GAA | GCC
Tyr   His   Asp   Phe   Ile   Cys   Asn   Trp   Leu   Gly   Asn   Lys   Ala   Trp   Thr   Glu   Ala

GGT | GAC | GCC | GAT
Gly   Asp   Ala   Asp
```

FIG. 2
(6 OF 6)

```
      1606           1615           1624           1633           1642           1651
      |              |              |              |              |              |
      CTT  GAG  TGG  CCC  GGA  CAG  GCT  GAA  TAT  GCC  TCC  GCT  AAG  CTG  GAG  GAC  CTG  GTC
      Leu  Glu  Trp  Pro  Gly  Gln  Ala  Glu  Tyr  Ala  Ser  Ala  Lys  Leu  Glu  Asp  Leu  Val
      1660                         1669                          1678                         1687                          1696                          1705
      |                            |                             |                            |                             |                             |
      GTG  GTC  GAG  AAT  GAG  CAC  AAG  AAG  GGC  AAG  ATC  GGC  CAG  GTC  AAG  TCC  CAT  GGC
      Val  Val  Glu  Asn  Glu  His  Lys  Lys  Gly  Lys  Ile  Gly  Gln  Val  Lys  Ser  His  Gly
      1714                         1723                          1732                          1741                         1750                          1759
      |                            |                             |                             |                            |                             |
      AAC  TTC  ACC  TTC  ATG  CGT  CTC  TAT  GGC  GGT  GGC  CAC  ATG  GTC  CCG  ATG  GAC  CAA
      Asn  Phe  Thr  Phe  MET  Arg  Leu  Tyr  Gly  Gly  Gly  His  MET  Val  Pro  MET  Asp  Gln
      1768                         1777                          1786                          1795                          1804                         1813
      |                            |                             |                             |                             |                            |
      CCC  GAG  TCG  AGT  CTT  GAA  TTC  TTC  AAC  CGC  TGG  TTG  GGA  GGT  GAA  TGG  TTT  TAA
      Pro  Glu  Ser  Ser  Leu  Glu  Phe  Phe  Asn  Arg  Trp  Leu  Gly  Gly  Glu  Trp  Phe
      1823           1833           1843           1853           1863           1873           1883
      AGACGTGCTA  TCACCGCATA  TAGACTTTCC  GGTCATTTCG  GTGACACTGC  AGATATGTTT  CTTAACGATA
      1893           1903           1913           1923           1933           1943           1953
      GTTTGAGGAT  GCTTGTCAAT  GCCCACTAAT  CCCGAGCCTT  ATGTTACATG  GTATCTATGA  GTTTGTCATT
      1963           1973           1983           1993           2002
      ATAGTGCATT  ATGCATTTGT  ACTCCGTACG  AGAATGAATC  AGCGGCCCGC
```

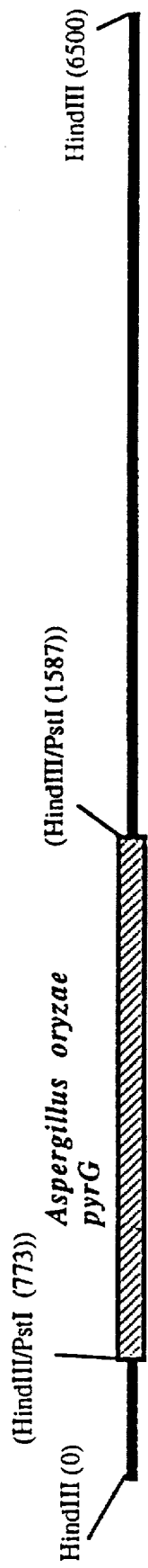

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 2068 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Aspergillus niger ( i x ) FEATURE:

( A ) NAME/KEY: intron
      ( B ) LOCATION: 572..632

( i x ) FEATURE:
      ( A ) NAME/KEY: CDS
      ( B ) LOCATION: join (571..633)

( x i ) SEQUENCE DESCRIPTION: SEQ ID NO: 1:

```
TCCTCTGCCT ACTCATCCCA TCACCATCTC AATTCATACC GCCCCCGTGG GGTTTCAGCA              60

CCA ATG AGA GTC CTT CCA GCT GCT ATG CTG GTT GGA GCG GCC ACG GCG             108
    Met Arg Val Leu Pro Ala Ala Met Leu Val Gly Ala Ala Thr Ala
    1           5                   10                  15

GCC GTT CCT CCC TTC CAG CAG GTC CTT GGA GGT AAC GGT GCC AAG CAC             156
Ala Val Pro Pro Phe Gln Gln Val Leu Gly Gly Asn Gly Ala Lys His
                20                  25                  30

GGT GCC GAC CAT GCG GCC GAG GTC CCT GCG GAT CAC AGT GCC GAC GGG             204
Gly Ala Asp His Ala Ala Glu Val Pro Ala Asp His Ser Ala Asp Gly
            35                  40                  45

TTC TCC AAG CCG CTG CAC GCA TTC CAG GAG GAG CTG AAG TCT CTC TCT             252
Phe Ser Lys Pro Leu His Ala Phe Gln Glu Glu Leu Lys Ser Leu Ser
        50                  55                  60

GAC GAG GCT CGT AAG CTT TGG GAT GAG GTG GCC AGC TTC TTC CCG GAG             300
Asp Glu Ala Arg Lys Leu Trp Asp Glu Val Ala Ser Phe Phe Pro Glu
    65                  70                  75

AGC ATG GAT CAG AAC CCT CTC TTT TCC CTC CCC AAG AAG CAC AAC CGC             348
Ser Met Asp Gln Asn Pro Leu Phe Ser Leu Pro Lys Lys His Asn Arg
80                  85                  90                  95

CGT CCC GAC TCG CAC TGG GAC CAC ATC GTC CGC GGC TCC GAC GTT CAG             396
Arg Pro Asp Ser His Trp Asp His Ile Val Arg Gly Ser Asp Val Gln
                100                 105                 110

AGC GTC TGG GTC ACT GGT GAG AAC GGT GAG AAG GAG CGC GAG GTC GAT             444
Ser Val Trp Val Thr Gly Glu Asn Gly Glu Lys Glu Arg Glu Val Asp
            115                 120                 125

GGC AAG CTG GAA GCC TAT GAT CTC AGG GTC AAG AAG ACC GAT CCT GGC             492
Gly Lys Leu Glu Ala Tyr Asp Leu Arg Val Lys Lys Thr Asp Pro Gly
        130                 135                 140

TCT CTT GGC ATC GAC CCC GGC GTG AAG CAG TAC ACC GGT TAT CTC GAT             540
Ser Leu Gly Ile Asp Pro Gly Val Lys Gln Tyr Thr Gly Tyr Leu Asp
    145                 150                 155

GAC AAC GAG AAT GAT AAG CAT TTG TTC TAC GTAAGCACAC CTTGGTTCAA               590
Asp Asn Glu Asn Asp Lys His Leu Phe Tyr
160                 165

GATCACGCTT TTTATATGCT CTGGATATCT AACGCAACTT AG TGG TTC TTC GAG              644
                                              Trp Phe Phe Glu
                                              170

TCT CGC AAT GAC CCC GAG AAT GAT CCC GTT GTT CTG TGG CTG AAC GGT             692
Ser Arg Asn Asp Pro Glu Asn Asp Pro Val Val Leu Trp Leu Asn Gly
    175                 180                 185

GGC CCT GGG TGC TCT TCC CTC ACC GGT CTC TTC ATG GAG CTT GGC CCT             740
Gly Pro Gly Cys Ser Ser Leu Thr Gly Leu Phe Met Glu Leu Gly Pro
190                 195                 200                 205

AGC AGC ATC AAC AAG AAG ATC CAG CCG GTC TAC AAT GAC TAC GCT TGG             788
Ser Ser Ile Asn Lys Lys Ile Gln Pro Val Tyr Asn Asp Tyr Ala Trp
                210                 215                 220

AAC TCC AAC GCG TCC GTG ATC TTC CTT GAC CAG CCT GTC AAT GTC GGT             836
Asn Ser Asn Ala Ser Val Ile Phe Leu Asp Gln Pro Val Asn Val Gly
            225                 230                 235

TAC TCC TAC AGT AAC TCT GCT GTC AGC GAC ACG GTC GCT GCT GGC AAG             884
Tyr Ser Tyr Ser Asn Ser Ala Val Ser Asp Thr Val Ala Ala Gly Lys
        240                 245                 250

GAC GTC TAT GCC TTG CTT ACC CTC TTC TTC AAA CAA TTC CCC GAG TAT             932
```

```
            Asp Val Tyr Ala Leu Leu Thr Leu Phe Phe Lys Gln Phe Pro Glu Tyr
                255                 260                 265
GCT AAG CAG GAC TTC CAC ATT GCC GGT GAA TCT TAT GCT GGT CAC TAT           980
Ala Lys Gln Asp Phe His Ile Ala Gly Glu Ser Tyr Ala Gly His Tyr
270                 275                 280                 285
ATC CCC GTC TTC GCT TCG GAG ATC CTG TCT CAC AAG AAG CGC AAC ATC          1028
Ile Pro Val Phe Ala Ser Glu Ile Leu Ser His Lys Lys Arg Asn Ile
                290                 295                 300
AAC CTG CAG TCC GTT CTC ATT GGC AAC GGT CTC ACC GAC GGA TAC ACC          1076
Asn Leu Gln Ser Val Leu Ile Gly Asn Gly Leu Thr Asp Gly Tyr Thr
            305                 310                 315
CAG TAC GAG TAC TAC CGT CCC ATG GCC TGC GGT GAC GGC GGT TAC CCA          1124
Gln Tyr Glu Tyr Tyr Arg Pro Met Ala Cys Gly Asp Gly Gly Tyr Pro
320                 325                 330
GCT GTC TTG GAC GAG AGC TCC TGC CAG TCC ATG GAC AAC GCT CTT CCT          1172
Ala Val Leu Asp Glu Ser Ser Cys Gln Ser Met Asp Asn Ala Leu Pro
        335                 340                 345
CGC TGC CAG TCT ATG ATT GAG TCT TGC TAC AGT TCC GAG AGC GCT TGG          1220
Arg Cys Gln Ser Met Ile Glu Ser Cys Tyr Ser Ser Glu Ser Ala Trp
350                 355                 360                 365
GTT TGT GTC CCG GCC TCC ATC TAC TGT AAC AAC GCC CTC CTT GCC CCT          1268
Val Cys Val Pro Ala Ser Ile Tyr Cys Asn Asn Ala Leu Leu Ala Pro
                370                 375                 380
TAC CAG CGC ACT GGG CAG AAC GTC TAT GAT GTC CGT GGT AAG TGC GAG          1316
Tyr Gln Arg Thr Gly Gln Asn Val Tyr Asp Val Arg Gly Lys Cys Glu
                385                 390                 395
GAT AGC TCT AAC CTT TGC TAC TCG GCT ATG GGC TAC GTC AGC GAC TAC          1364
Asp Ser Ser Asn Leu Cys Tyr Ser Ala Met Gly Tyr Val Ser Asp Tyr
            400                 405                 410
CTG AAC AAG CCC GAA GTC ATC GAG GCT GTT GGC GCT GAG GTC AAC GGC          1412
Leu Asn Lys Pro Glu Val Ile Glu Ala Val Gly Ala Glu Val Asn Gly
        415                 420                 425
TAC GAC TCG TGC AAC TTT GAC ATC AAC CGC AAC TTC CTC TTC CAC GGT          1460
Tyr Asp Ser Cys Asn Phe Asp Ile Asn Arg Asn Phe Leu Phe His Gly
430                 435                 440                 445
GAC TGG ATG AAG CCC TAC CAC CGC CTC GTT CCG GGA CTC CTG GAG CAG          1508
Asp Trp Met Lys Pro Tyr His Arg Leu Val Pro Gly Leu Leu Glu Gln
                450                 455                 460
ATC CCT GTC TTG ATC TAT GCC GGT GAT GCT GAT TTC ATT TGC AAC TGG          1556
Ile Pro Val Leu Ile Tyr Ala Gly Asp Ala Asp Phe Ile Cys Asn Trp
                465                 470                 475
CTG GGC AAC AAG GCC TGG ACT GAA GCC CTG GAG TGG CCC GGA CAG GCT          1604
Leu Gly Asn Lys Ala Trp Thr Glu Ala Leu Glu Trp Pro Gly Gln Ala
        480                 485                 490
GAA TAT GCC TCC GCT GAG CTG GAG GAT CTG GTC ATT GTC GAC AAT GAG          1652
Glu Tyr Ala Ser Ala Glu Leu Glu Asp Leu Val Ile Val Asp Asn Glu
495                 500                 505
CAC ACG GGC AAG AAG ATT GGC CAG GTT AAG TCC CAT GGC AAC TTC ACC          1700
His Thr Gly Lys Lys Ile Gly Gln Val Lys Ser His Gly Asn Phe Thr
510                 515                 520                 525
TTC ATG CGT CTC TAT GGT GGT GGC CAC ATG GTC CCG ATG GAC CAG CCC          1748
Phe Met Arg Leu Tyr Gly Gly Gly His Met Val Pro Met Asp Gln Pro
                530                 535                 540
GAG TCG AGT CTC GAG TTC TTC AAC CGC TGG TTG GGA GGT GAA TGG TTC          1796
Glu Ser Ser Leu Glu Phe Phe Asn Arg Trp Leu Gly Gly Glu Trp Phe
            545                 550                 555
TAA AGACGTGCTA CCACCGCATA TAGACTTTCT GGTCATTTCG GTGACACTGC               1849
AGATATGTTT CTTAACGATA GTTTGAGCAT GCTTGTCAAT GCCCACTAGT CCCGATCCTT        1909
ATATGTTGCA TGGTATCTAT GAGTTTTGTC ACTATAGTGC ATTATACATG TGTACTTCGT        1969
```

```
ATGAGAATGA ATCGATCGCA TTTACACGCA TATAAATAGT ACCCACCTCC GCCTGGACAT    2029

GAATTAGGCC CGGCCAGTCG TTTACATACA GTGCTAGAA                          2068
```

( 2 ) INFORMATION FOR SEQ ID NO: 2:

( i ) SEQUENCE CHARACTERISTICS:
    ( A ) LENGTH: 557 amino acids
    ( B ) TYPE: amino acid
    ( C ) STRANDEDNESS: single
    ( D ) TOPOLOGY: linear ( i i ) MOLECULE TYPE: protein ( v i ) ORIGINAL SOURCE:
    ( A ) ORGANISM: Aspergillus Niger ( x i ) SEQUENCE DESCRIPTION: SEQ ID NO: 2:

```
Met  Arg  Val  Leu  Pro  Ala  Ala  Met  Leu  Val  Gly  Ala  Ala  Thr  Ala  Ala
1              5                   10                  15

Val  Pro  Pro  Phe  Gln  Gln  Val  Leu  Gly  Gly  Asn  Gly  Ala  Lys  His  Gly
               20                  25                  30

Ala  Asp  His  Ala  Ala  Glu  Val  Pro  Ala  Asp  His  Ser  Ala  Asp  Gly  Phe
          35                  40                  45

Ser  Lys  Pro  Leu  His  Ala  Phe  Gln  Glu  Glu  Leu  Lys  Ser  Leu  Ser  Asp
     50                  55                  60

Glu  Ala  Arg  Lys  Leu  Trp  Asp  Glu  Val  Ala  Ser  Phe  Phe  Pro  Glu  Ser
65                  70                  75                       80

Met  Asp  Gln  Asn  Pro  Leu  Phe  Ser  Leu  Pro  Lys  Lys  His  Asn  Arg  Arg
                    85                  90                  95

Pro  Asp  Ser  His  Trp  Asp  His  Ile  Val  Arg  Gly  Ser  Asp  Val  Gln  Ser
               100                 105                 110

Val  Trp  Val  Thr  Gly  Glu  Asn  Gly  Glu  Lys  Glu  Arg  Glu  Val  Asp  Gly
          115                 120                 125

Lys  Leu  Glu  Ala  Tyr  Asp  Leu  Arg  Val  Lys  Lys  Thr  Asp  Pro  Gly  Ser
     130                 135                 140

Leu  Gly  Ile  Asp  Pro  Gly  Val  Lys  Gln  Tyr  Thr  Gly  Tyr  Leu  Asp  Asp
145                 150                 155                      160

Asn  Glu  Asn  Asp  Lys  His  Leu  Phe  Tyr  Trp  Phe  Phe  Glu  Ser  Arg  Asn
                    165                 170                 175

Asp  Pro  Glu  Asn  Asp  Pro  Val  Val  Leu  Trp  Leu  Asn  Gly  Gly  Pro  Gly
               180                 185                 190

Cys  Ser  Ser  Leu  Thr  Gly  Leu  Phe  Met  Glu  Leu  Gly  Pro  Ser  Ser  Ile
          195                 200                 205

Asn  Lys  Lys  Ile  Gln  Pro  Val  Tyr  Asn  Asp  Tyr  Ala  Trp  Asn  Ser  Asn
     210                 215                 220

Ala  Ser  Val  Ile  Phe  Leu  Asp  Gln  Pro  Val  Asn  Val  Gly  Tyr  Ser  Tyr
225                 230                 235                      240

Ser  Asn  Ser  Ala  Val  Ser  Asp  Thr  Val  Ala  Ala  Gly  Lys  Asp  Val  Tyr
                    245                 250                 255

Ala  Leu  Leu  Thr  Leu  Phe  Phe  Lys  Gln  Phe  Pro  Glu  Tyr  Ala  Lys  Gln
               260                 265                 270

Asp  Phe  His  Ile  Ala  Gly  Glu  Ser  Tyr  Ala  Gly  His  Tyr  Ile  Pro  Val
          275                 280                 285

Phe  Ala  Ser  Glu  Ile  Leu  Ser  His  Lys  Lys  Arg  Asn  Ile  Asn  Leu  Gln
     290                 295                 300

Ser  Val  Leu  Ile  Gly  Asn  Gly  Leu  Thr  Asp  Gly  Tyr  Thr  Gln  Tyr  Glu
305                 310                 315                      320
```

```
Tyr Tyr Arg Pro Met Ala Cys Gly Asp Gly Gly Tyr Pro Ala Val Leu
            325             330             335
Asp Glu Ser Ser Cys Gln Ser Met Asp Asn Ala Leu Pro Arg Cys Gln
            340             345             350
Ser Met Ile Glu Ser Cys Tyr Ser Ser Glu Ser Ala Trp Val Cys Val
            355             360             365
Pro Ala Ser Ile Tyr Cys Asn Asn Ala Leu Leu Ala Pro Tyr Gln Arg
            370             375             380
Thr Gly Gln Asn Val Tyr Asp Val Arg Gly Lys Cys Glu Asp Ser Ser
385             390             395             400
Asn Leu Cys Tyr Ser Ala Met Gly Tyr Val Ser Asp Tyr Leu Asn Lys
            405             410             415
Pro Glu Val Ile Glu Ala Val Gly Ala Glu Val Asn Gly Tyr Asp Ser
            420             425             430
Cys Asn Phe Asp Ile Asn Arg Asn Phe Leu Phe His Gly Asp Trp Met
            435             440             445
Lys Pro Tyr His Arg Leu Val Pro Gly Leu Leu Glu Gln Ile Pro Val
            450             455             460
Leu Ile Tyr Ala Gly Asp Ala Asp Phe Ile Cys Asn Trp Leu Gly Asn
465             470             475             480
Lys Ala Trp Thr Glu Ala Leu Glu Trp Pro Gly Gln Ala Glu Tyr Ala
            485             490             495
Ser Ala Glu Leu Glu Asp Leu Val Ile Val Asp Asn Glu His Thr Gly
            500             505             510
Lys Lys Ile Gly Gln Val Lys Ser His Gly Asn Phe Thr Phe Met Arg
            515             520             525
Leu Tyr Gly Gly Gly His Met Val Pro Met Asp Gln Pro Glu Ser Ser
530             535             540
Leu Glu Phe Phe Asn Arg Trp Leu Gly Gly Glu Trp Phe
545             550             555
```

( 2 ) INFORMATION FOR SEQ ID NO: 3:

( i ) SEQUENCE CHARACTERISTICS:
        ( A ) LENGTH: 2002 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Aspergillus niger ( i x ) FEATURE:
        ( A ) NAME/KEY: intron
        ( B ) LOCATION: 349..411

( i x ) FEATURE:
        ( A ) NAME/KEY: CDS
        ( B ) LOCATION: join (348..412)

( x i ) SEQUENCE DESCRIPTION: SEQ ID NO: 3:

```
GCGGCCGCTG CTACTTGCTT TTTCTAATTT GATACTTTTG TGTCCGTACC GTACCTTCCA        60

GACCGCAAGG TACCCATCCT CTACCTACTC ATCCCATCAT CATCTCGATT TCATACCAAC       120

CCCGTTGGGT TTCAACACA ATG AGA GTT CTT CCA GCT GCT ATG CTG GTT GGA       172
                     Met Arg Val Leu Pro Ala Ala Met Leu Val Gly
                      1               5                      10

GCG GGC ACT GCG GCC GTC CCT CCC TTC CAG CAG GTC CTT GGA GGT AAC       220
Ala Gly Thr Ala Ala Val Pro Pro Phe Gln Gln Val Leu Gly Gly Asn
```

```
                    15                        20                        25
GGT GCC AAG CAC GGT GCC GAC CAT GCG GCC GAG GTC CCT GCG GAT CAC       268
Gly Ala Lys His Gly Ala Asp His Ala Ala Glu Val Pro Ala Asp His
         30                  35                  40

AGT GCC GAC GGG TTC TCC AAG CCG CTG CAC GCA TTC CAG GAG GAG CTG       316
Ser Ala Asp Gly Phe Ser Lys Pro Leu His Ala Phe Gln Glu Glu Leu
         45                  50                  55

AAG TCT CTC TCT GAT GAG GCT CGT AAG CTC TGG GAT GAG GTT GCT AGC       364
Lys Ser Leu Ser Asp Glu Ala Arg Lys Leu Trp Asp Glu Val Ala Ser
60                   65                  70                  75

TTC TTC CCG GAG AGC ATG GAT CAG AAC CCT CTC TTC TCC CTC CCC AAG       412
Phe Phe Pro Glu Ser Met Asp Gln Asn Pro Leu Phe Ser Leu Pro Lys
                 80                  85                  90

AAG CAC AAC CGC CGC CCC GAC CAC CAC TGG GAC CAC ATC GTC CGC GGC       460
Lys His Asn Arg Arg Pro Asp His His Trp Asp His Ile Val Arg Gly
                 95                 100                 105

TCC GAC GTT CAG AGC GTC TGG GTT ACT GGT GAG AAC GGT GAG AAG GAG       508
Ser Asp Val Gln Ser Val Trp Val Thr Gly Glu Asn Gly Glu Lys Glu
                110                 115                 120

CGT GAG GTC GAT GGC AAG CTG GAA GCC TAT GAT CTC AGG GTC AAG AAG       556
Arg Glu Val Asp Gly Lys Leu Glu Ala Tyr Asp Leu Arg Val Lys Lys
        125                 130                 135

ACC GAT CCT AGC TCT CTT GGC ATC GAC CCT GGC GTA AAG CAG TAC ACC       604
Thr Asp Pro Ser Ser Leu Gly Ile Asp Pro Gly Val Lys Gln Tyr Thr
140                 145                 150                 155

GGT TAT CTC GAT GAC AAC GAG AAC GAC AAG CAT CTG TTC TAC TGG TTC       652
Gly Tyr Leu Asp Asp Asn Glu Asn Asp Lys His Leu Phe Tyr Trp Phe
                160                 165                 170

TTC GAG TCT CGC AAT GAC CCC GAG AAT GAC CCT GTT GTT CTG TGG CTG       700
Phe Glu Ser Arg Asn Asp Pro Glu Asn Asp Pro Val Val Leu Trp Leu
        175                 180                 185

AAC GGT GGC CCT GGA TGC TCT TCC CTC ACC GGT CTT TTC ATG GAG CTC       748
Asn Gly Gly Pro Gly Cys Ser Ser Leu Thr Gly Leu Phe Met Glu Leu
        190                 195                 200

GGC CCT AGC AGC ATC AAC AAG AAG ATC CAG CCG GTC TAC AAC GAC TAC       796
Gly Pro Ser Ser Ile Asn Lys Lys Ile Gln Pro Val Tyr Asn Asp Tyr
    205                 210                 215

GCT TGG AAC TCC AAC GCG TCC GTG ATC TTC CTT GAC CAG CCT GTC AAC       844
Ala Trp Asn Ser Asn Ala Ser Val Ile Phe Leu Asp Gln Pro Val Asn
220                 225                 230                 235

GTC GGT TAC TCT TAC AGC AAC TCT GCT GTC AGC GAC ACC GTT GCT GCT       892
Val Gly Tyr Ser Tyr Ser Asn Ser Ala Val Ser Asp Thr Val Ala Ala
                240                 245                 250

GGC AAG GAC GTC TAT GCC TTG CTT ACC CTC TTC TTC AAA CAA TTC CCC       940
Gly Lys Asp Val Tyr Ala Leu Leu Thr Leu Phe Phe Lys Gln Phe Pro
        255                 260                 265

GAG TAT GCC AAG CAG GAC TTC CAC ATT GCC GGT GAA TCC TAT GCT GGT       988
Glu Tyr Ala Lys Gln Asp Phe His Ile Ala Gly Glu Ser Tyr Ala Gly
        270                 275                 280

CAC TAT ATC CCC GTC TTT GCT TCG GAG ATT TTG TCT CAC AAG AAG CGC      1036
His Tyr Ile Pro Val Phe Ala Ser Glu Ile Leu Ser His Lys Lys Arg
    285                 290                 295

AAC ATC AAC CTG CAG TCC GTT CTT ATT GGC AAC GGT CTC ACC GAC GGT      1084
Asn Ile Asn Leu Gln Ser Val Leu Ile Gly Asn Gly Leu Thr Asp Gly
300                 305                 310                 315

CTC ACT CAG TAC GAG TAC TAC CGT CCC ATG GCC TGT GGT GAC GGT GGT      1132
Leu Thr Gln Tyr Glu Tyr Tyr Arg Pro Met Ala Cys Gly Asp Gly Gly
                320                 325                 330

TAC CCA GCT GTC TTG GAC GAG GGC TCC TGC CAG GCC ATG GAC AAC GCC      1180
Tyr Pro Ala Val Leu Asp Glu Gly Ser Cys Gln Ala Met Asp Asn Ala
```

| | | | | | | | | | | | | | | | | |
|---|---|---|---|---|---|---|---|---|---|---|---|---|---|---|---|---|
| | | | 335 | | | | 340 | | | | | 345 | | | | |
| CTT | CCT | CGC | TGC | CAG | TCT | ATG | ATT | GAG | TCT | TGC | TAT | AGT | TCC | GAG | AGC | 1228 |
| Leu | Pro | Arg | Cys | Gln | Ser | Met | Ile | Glu | Ser | Cys | Tyr | Ser | Ser | Glu | Ser | |
| | 350 | | | | | 355 | | | | | 360 | | | | | |
| GCT | TGG | GTT | TGT | GTC | CCG | GCC | TCC | ATC | TAC | TGT | AAC | AAC | GCC | CTC | CTT | 1276 |
| Ala | Trp | Val | Cys | Val | Pro | Ala | Ser | Ile | Tyr | Cys | Asn | Asn | Ala | Leu | Leu | |
| | 365 | | | | | 370 | | | | | 375 | | | | | |
| GCC | CCT | TAC | CAG | CGC | ACC | GGA | CAG | AAC | GTC | TAC | GAT | GTT | CGT | GGT | AAG | 1324 |
| Ala | Pro | Tyr | Gln | Arg | Thr | Gly | Gln | Asn | Val | Tyr | Asp | Val | Arg | Gly | Lys | |
| 380 | | | | | 385 | | | | | 390 | | | | | 395 | |
| TGC | GAG | GAT | AGC | TCC | AAC | CTC | TGC | TAC | TCG | GCC | ATG | GGC | TAC | GTC | AGC | 1372 |
| Cys | Glu | Asp | Ser | Ser | Asn | Leu | Cys | Tyr | Ser | Ala | Met | Gly | Tyr | Val | Ser | |
| | | | | 400 | | | | | 405 | | | | | 410 | | |
| GAC | TAC | CTG | AAC | AAG | ACC | GAG | GTC | ATT | GAG | GCT | GTT | GGC | GCT | GAG | GTC | 1420 |
| Asp | Tyr | Leu | Asn | Lys | Thr | Glu | Val | Ile | Glu | Ala | Val | Gly | Ala | Glu | Val | |
| | | | 415 | | | | 420 | | | | | 425 | | | | |
| AAC | GGC | TAC | GAC | TCG | TGC | AAC | TTT | GAC | ATC | AAC | CGC | AAC | TTC | CTC | TTC | 1468 |
| Asn | Gly | Tyr | Asp | Ser | Cys | Asn | Phe | Asp | Ile | Asn | Arg | Asn | Phe | Leu | Phe | |
| | | 430 | | | | | 435 | | | | | 440 | | | | |
| CAC | GGT | GAC | TGG | ATG | AAG | CCC | TAC | CAC | CGT | CTC | GTT | CCG | GGA | CTC | CTG | 1516 |
| His | Gly | Asp | Trp | Met | Lys | Pro | Tyr | His | Arg | Leu | Val | Pro | Gly | Leu | Leu | |
| | 445 | | | | | 450 | | | | | 455 | | | | | |
| GAG | CAG | ATC | CCT | GTC | CTG | ATC | TAC | GCT | GGT | GAC | GCC | GAT | TTC | ATC | TGC | 1564 |
| Glu | Gln | Ile | Pro | Val | Leu | Ile | Tyr | Ala | Gly | Asp | Ala | Asp | Phe | Ile | Cys | |
| 460 | | | | | 465 | | | | | 470 | | | | | 475 | |
| AAC | TGG | CTG | GGC | AAC | AAG | GCC | TGG | ACT | GAA | GCC | CTT | GAG | TGG | CCC | GGA | 1612 |
| Asn | Trp | Leu | Gly | Asn | Lys | Ala | Trp | Thr | Glu | Ala | Leu | Glu | Trp | Pro | Gly | |
| | | | | 480 | | | | | 485 | | | | | 490 | | |
| CAG | GCT | GAA | TAT | GCC | TCC | GCT | AAG | CTG | GAG | GAC | CTG | GTC | GTG | GTC | GAG | 1660 |
| Gln | Ala | Glu | Tyr | Ala | Ser | Ala | Lys | Leu | Glu | Asp | Leu | Val | Val | Val | Glu | |
| | | | 495 | | | | | 500 | | | | | 505 | | | |
| AAT | GAG | CAC | AAG | GGC | AAG | AAG | ATC | GGC | CAG | GTC | AAG | TCC | CAT | GGC | AAC | 1708 |
| Asn | Glu | His | Lys | Gly | Lys | Lys | Ile | Gly | Gln | Val | Lys | Ser | His | Gly | Asn | |
| | | 510 | | | | | 515 | | | | | 520 | | | | |
| TTC | ACC | TTC | ATG | CGT | CTC | TAT | GGC | GGT | GGC | CAC | ATG | GTC | CCG | ATG | GAC | 1756 |
| Phe | Thr | Phe | Met | Arg | Leu | Tyr | Gly | Gly | Gly | His | Met | Val | Pro | Met | Asp | |
| | 525 | | | | | 530 | | | | | 535 | | | | | |
| CAA | CCC | GAG | TCG | AGT | CTT | GAA | TTC | TTC | AAC | CGC | TGG | TTG | GGA | GGT | GAA | 1804 |
| Gln | Pro | Glu | Ser | Ser | Leu | Glu | Phe | Phe | Asn | Arg | Trp | Leu | Gly | Gly | Glu | |
| 540 | | | | | 545 | | | | | 550 | | | | | 555 | |

```
TGG TTT TAA AGACGTGCTA TCACCGCATA TAGACTTTCC GGTCATTTCG GTGACACTGC  1863
Trp Phe
AGATATGTTT CTTAACGATA GTTTGAGGAT GCTTGTCAAT GCCCACTAAT CCCGAGCCTT  1923

ATGTTACATG GTATCTATGA GTTTGTCATT ATAGTGCATT ATGCATTTGT ACTCCGTACG  1983

AGAATGAATC AGCGGCCGC                                                 2002
```

( 2 ) INFORMATION FOR SEQ ID NO: 4:

( i ) SEQUENCE CHARACTERISTICS:
        ( A ) LENGTH: 557 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Aspergillus Niger ( x i ) SEQUENCE DESCRIPTION: SEQ ID NO: 4:

```
Met Arg Val Leu Pro Ala Ala Met Leu Val Gly Ala Gly Thr Ala Ala
1               5                   10                  15
```

```
Val Pro Pro Phe Gln Gln Val Leu Gly Asn Gly Ala Lys His Gly
                20                  25                  30
Ala Asp His Ala Ala Glu Val Pro Ala Asp His Ser Ala Asp Gly Phe
            35                  40                  45
Ser Lys Pro Leu His Ala Phe Gln Glu Glu Leu Lys Ser Leu Ser Asp
    50                  55                  60
Glu Ala Arg Lys Leu Trp Asp Glu Val Ala Ser Phe Phe Pro Glu Ser
65                  70                  75                  80
Met Asp Gln Asn Pro Leu Phe Ser Leu Pro Lys Lys His Asn Arg Arg
                85                  90                  95
Pro Asp His His Trp Asp His Ile Val Arg Gly Ser Asp Val Gln Ser
            100                 105                 110
Val Trp Val Thr Gly Glu Asn Gly Glu Lys Glu Arg Glu Val Asp Gly
            115                 120                 125
Lys Leu Glu Ala Tyr Asp Leu Arg Val Lys Lys Thr Asp Pro Ser Ser
130                 135                 140
Leu Gly Ile Asp Pro Gly Val Lys Gln Tyr Thr Gly Tyr Leu Asp Asp
145                 150                 155                 160
Asn Glu Asn Asp Lys His Leu Phe Tyr Trp Phe Phe Glu Ser Arg Asn
                165                 170                 175
Asp Pro Glu Asn Asp Pro Val Val Leu Trp Leu Asn Gly Gly Pro Gly
            180                 185                 190
Cys Ser Ser Leu Thr Gly Leu Phe Met Glu Leu Gly Pro Ser Ser Ile
            195                 200                 205
Asn Lys Lys Ile Gln Pro Val Tyr Asn Asp Tyr Ala Trp Asn Ser Asn
    210                 215                 220
Ala Ser Val Ile Phe Leu Asp Gln Pro Val Asn Val Gly Tyr Ser Tyr
225                 230                 235                 240
Ser Asn Ser Ala Val Ser Asp Thr Val Ala Ala Gly Lys Asp Val Tyr
                245                 250                 255
Ala Leu Leu Thr Leu Phe Phe Lys Gln Phe Pro Glu Tyr Ala Lys Gln
            260                 265                 270
Asp Phe His Ile Ala Gly Glu Ser Tyr Ala Gly His Tyr Ile Pro Val
        275                     280                 285
Phe Ala Ser Glu Ile Leu Ser His Lys Lys Arg Asn Ile Asn Leu Gln
    290                 295                 300
Ser Val Leu Ile Gly Asn Gly Leu Thr Asp Gly Leu Thr Gln Tyr Glu
305                 310                 315                 320
Tyr Tyr Arg Pro Met Ala Cys Gly Asp Gly Gly Tyr Pro Ala Val Leu
                325                 330                 335
Asp Glu Gly Ser Cys Gln Ala Met Asp Asn Ala Leu Pro Arg Cys Gln
            340                 345                 350
Ser Met Ile Glu Ser Cys Tyr Ser Ser Glu Ser Ala Trp Val Cys Val
        355                 360                 365
Pro Ala Ser Ile Tyr Cys Asn Asn Ala Leu Leu Ala Pro Tyr Gln Arg
    370                 375                 380
Thr Gly Gln Asn Val Tyr Asp Val Arg Gly Lys Cys Glu Asp Ser Ser
385                 390                 395                 400
Asn Leu Cys Tyr Ser Ala Met Gly Tyr Val Ser Asp Tyr Leu Asn Lys
                405                 410                 415
Thr Glu Val Ile Glu Ala Val Gly Ala Glu Val Asn Gly Tyr Asp Ser
            420                 425                 430
Cys Asn Phe Asp Ile Asn Arg Asn Phe Leu Phe His Gly Asp Trp Met
```

|     | 435 |     |     |     |     | 440 |     |     |     |     | 445 |     |     |     |
| --- | --- | --- | --- | --- | --- | --- | --- | --- | --- | --- | --- | --- | --- | --- |
| Lys | Pro 450 | Tyr | His | Arg | Leu | Val 455 | Pro | Gly | Leu | Leu | Glu 460 | Gln | Ile | Pro | Val |
| Leu 465 | Ile | Tyr | Ala | Gly | Asp 470 | Ala | Asp | Phe | Ile | Cys 475 | Asn | Trp | Leu | Gly | Asn 480 |
| Lys | Ala | Trp | Thr | Glu 485 | Ala | Leu | Glu | Trp | Pro 490 | Gly | Gln | Ala | Glu | Tyr 495 | Ala |
| Ser | Ala | Lys | Leu 500 | Glu | Asp | Leu | Val | Val 505 | Val | Glu | Asn | Glu | His 510 | Lys | Gly |
| Lys | Lys | Ile 515 | Gly | Gln | Val | Lys | Ser 520 | His | Gly | Asn | Phe | Thr 525 | Phe | Met | Arg |
| Leu | Tyr 530 | Gly | Gly | Gly | His | Met 535 | Val | Pro | Met | Asp | Gln 540 | Pro | Glu | Ser | Ser |
| Leu 545 | Glu | Phe | Phe | Asn | Arg 550 | Trp | Leu | Gly | Gly | Glu 555 | Trp | Phe |     |     |     |

GENE ENCODING CARBOXYPEPTIDASE OF *ASPERGILLUS NIGER*

This is a divisional application of application Ser. No. 08/309,341, filed Sep. 20, 1994, now U.S. Pat. No. 5,594,119 the contents of which are incorporated herein by reference in their entirety.

FIELD OF THE INVENTION

The present invention relates to a gene encoding a fungal vacuolar protease. In particular, the invention relates to a carboxypeptidase gene of a filamentous ascomycete or deuteromycete fungus, such as those of the genus Aspergillus.

BACKGROUND OF THE INVENTION

The fungal vacuole is an acidic organelle that contains many hydrolases, including several proteases, and is essentially equivalent to the mammalian lysosome. Several of the hydrolases have been identified and characterized in one or more species of fungi, particularly in yeast; these include protease A(PEP4 or PrA), protease B(PrB), aminopeptidase (APE), dipeptidyl aminopeptidase B(DPAP B), carboxypeptidase Y(CPY), and carboxypeptidase S(CPS). Most of the vacuolar hydrolases are glycoproteins which are synthesized as inactive precursors. In fact, all the aforementioned proteases with the exception of APE have signal peptides that lead to transit through the secretory pathway. In the late golgi, vacuolar proteins are sorted from secretory proteins and eventually delivered to the vacuole. In addition to a signal peptide, most vacuolar proteins also have a propeptide which is cleaved upon delivery to the vacuole to generate the mature active enzyme. It has been demonstrated that the amino acid information in PrA and CPY required for vacuolar targeting is present within the propeptide(Johnson et al., Cell 48: 875–885, 1987; Rothman et al. PNAS USA 83: 3248–3252, 1989; Valls et al., Cell 48: 887–897, 1989; Valls et al. J. Cell Biol. 111: 361–368, 1987). For CPY a string of four amino acid residues (QRPL) has been shown to be required for localization to the vacuole (Valls et al., J. Cell Biol. 111: 361–368, 1990). Once delivered to the vacuole, proteinase A (pep4)cleaves the propeptide of CPY and PrB leading to the activation of the proteases (Ammerer et al., Mol. Cell. Biol. 6: 2490–2499, 1986; Woolford et al., Mol. Cell. Biol. 6: 2500–2510, 1986).

In *S. cerevisiae*, three classes of mutants which mislocalize or missort vacuolar proteins have been identified (Bankaitis et al., PNAS USA 83: 9075–9079, 1986; Robinson et al., Mol. Cell. Biol., 8: 4936–4948, 1988; Rothman et al., EMBO J. 8: 2057–2065, 1989; Rothman and Stevens, Cell 47: 1041–1051, 1986). These mutants are called vps or vacuolar protein sorting mutants. Several of these mutants are isolated using a selection based on the observation that overexpression of a vacuolar protease due to a high copy number on a plasmid leads to a secretion of vacuolar proteases (Stevens et al., J. Cell Biol. 102: 1551–1557, 1986; Rothman et al, PNAS USA 83: 3248–3242, 1986). This suggests that it is possible to saturate the sorting machinery within the late golgi.

In *S. cerevisiae*, it has also been demonstrated that strains deleted for PEP4, CPY and PrB produce higher levels of heterologous proteins due to a decrease in proteolysis of the desired product. Therefore, the vacuolar proteases in question are important from a commercial point of view because many of the fungi which produce them are used for recombinant production of heterologous proteins. The presence of these proteases in fermentation is undesirable, in that they can degrade the protein of interest, thereby significantly reducing yield. Elimination of the function of any given protease is facilitated by the disruption or deletion of the gene encoding it; however, doing so first requires identification and isolation of the corresponding gene in the host species of interest. As noted above, a few such genes have been isolated from various yeast strains; however, the genes encoding vacuolar proteases in the filamentous ascomycetes or deuteromycetes are less well known. For example, PEPC (Frederick et al., Gene 125: 57–64, 1993) and PEPE (Jarai et al., Gene 145: 171–178, 1994) genes coding for two other vacuolar proteases from *Aspergilus niger* have been isolated. PEPC codes for a proteinase B(PrB) homologue, and PEPE codes for a proteinase A homologue. The gene PEP4 from *Neurospora crassa* coding for a PrA homologue has also been cloned(Bowman, 17th Fungal Genetics Conference, 1993). For the first time herein is described the gene encoding a vacuolar CPY from a filamentous ascomycete or deuteromycete.

SUMMARY OF THE INVENTION

The present invention relates to a nucleic acid construct comprising a sequence encoding a filamentous ascomycete or deuteromycete carboxypeptidase Y, as well as the recombinantly produced protein encoded thereby. As used herein, "nucleic acid construct" is intended to indicate any nucleic acid molecule of cDNA, genomic DNA, synthetic DNA or RNA origin. The term "construct" is intended to indicated a nucleic acid segment which may be single-or double-stranded, and which may be isolated in complete or partial form from a naturally occurring gene or which has been modified to contain segments of DNA which are combined and juxtaposed in a manner which would not otherwise exist in nature. The construct may optionally contain other nucleic acid segments. In a preferred embodiment, the sequence encodes a carboxypeptidase of the genus Aspergillus. The invention also provides a method for producing a non-carboxypeptidase-producing filamentous ascomycete or deuteromycete cell, which comprises disrupting or deleting the carboxypeptidase gene so as to prevent the expression of a functional enzyme, or treating the gene by classical mutagenesis using physical or chemical treatments to generate cells which are reduced or lacking in their ability to produce CPY. In addition, the invention also encompasses a filamentous ascomycete or deuteromycete which is unable to produce a functional carboxypeptidase enzyme, or which produces the carboxypeptidase in reduced amounts relative to the amount produced by the wild-type strain. Such organisms provide the basis for an improved method of recombinant protein production, wherein the carboxypeptidase-deficient microorganism is transformed with the nucleic acid construct encoding the protein of interest, and cultured under conditions conducive to the expression of the protein.

BRIEF DESCRIPTION OF THE FIGURES

FIG. 1 illustrates the DNA sequence and translation of the *A. niger* Bo-1 genomic CPY clone.

FIG. 2 illustrates the DNA sequence and translation of *A. niger* SFAG 2 CPY cDNA. The predicted site for signal peptidase cleavage and the N-terminus of mature CPY are indicated.

FIG. 3 illustrates the construct used in disruption CPY.

DETAILED DESCRIPTION OF THE INVENTION

Attempts to isolate an Aspergillus carboxypeptidase Y are initiated by designing a series of degenerate oligonucleotides, using the sequences of *S. cerevisiae* CPY, *Penicillium janthinellum* carboxypeptidase S1(Svedsen et al., FEBS 333: 39–43, 1993, and malt carboxypeptidase-MIII(Sørensen et al., Carlsberg Res. Commun. 54: 193–202, 1993). The oligonucleotide sequences are provided the examples below. These sequences are used as primers in various combinations in a PCR reaction using *Aspergillus niger* strain Bo-1 genomic DNA as a template. Two of the reactions(with primers 1-1 and 2-1; and 1-2 and 2-2) yield an 1100 bp amplification product, which is subcloned and sequenced, but none of the subclones has significant homology to CPY to be identified as the gene of interest.

Further PCR reactions with primers 3-1, 3-2, 4-1, 4-2, 2-1 and 2-2 are then made in two of the reactions(primers 4-1 and 2-1; and 4-2 and 2-1) a 600 bp amplification product is obtained. This product is subcloned and 11 of the subclones sequenced; nine of these subclones are identical, and have homology to carboxypeptidaseY genes from other sources. The insert from one of the subclones is used to probe *A. niger* genomic DNA; hybridization with single bands is observed with BamHI, HindIII, and SalI digests, suggesting that a single CPY gene exists in *A. niger*. Hybridizations are done at 65° C. in 1.5×SSPE, 1.0% SDS, 0.5% non-fat milk and 200 µg/ml salmon sperm DNA.

An *A. niger* genomic DNA bank in EMBL4 is prepared and probed with the PCR CPY-derived gene fragment ($^{32}$P-labeled), in order to isolate a full length gene. Out of approximately 28,000 plaques, 11 positives are picked; nine of these still hybridize with the probe after purification. A 5.5 HindIII fragment common to a majority of these clones is identified as the *A. niger* CPY gene. This fragment is subcloned and sequenced; the sequence of the fragment, including the CPY coding region and predicted amino acid sequence, is provided in FIG. 1.

Subsequently, a cDNA bank from a different *A. niger* strain is also screened. At least one full-length clone is identified from this library as well. This clone is sequenced and the sequence is depicted in FIG. 2. Both DNA sequences predict a CPY precursor of 557 amino acids in length. Based on a comparison with the homologous gene from *S. cerevisiae*, CPY from *A. niger* appears to have a prepropeptide of 137 or 138 amino acids. The gene contains one intron of 61 base pairs. A comparison of the two *A. niger* sequences will show some difference in amino acid sequence, which presumably reflects the different strains from which the genomic and cDNA clones are isolated. A comparison with the amino acid sequences of the corresponding CPY genes of *S. cerevisiae* and *C. albicans* shows a 65% and 66% identity, respectively.

The present invention is not limited to the use of the sequences disclosed in FIGS. 1 and 2. First, the invention also encompasses nucleotide sequences which produce the same amino acid sequence as depicted in FIG. 1 or 2, but differ by virtue of the degeneracy of the genetic code. In addition, the difference in amino acid sequence shown for two strains of the same species shows that variation within the sequence of a single species is tolerated, and using the techniques described herein, such variants can readily be identified. Therefore, when "*A. niger*" is referred to in this context, it will be understood to encompass all such variations. In particular, the invention also encompasses any variant nucleotide sequence, and the protein encoded thereby, which protein retains at least about an 80%, preferably about 85%, and most preferably at least about 90–95% homology with the amino acid sequence depicted in FIGS. 1 or 2, and which qualitatively retains the activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Ash and Gln.

In addition, the isolated gene provides a means for isolating homologous genes from other filamentous ascomycetes or deuteromycetes, such as other Aspergillus species, e.g., *A. oryzae, A. foetidus, A. japonicus, A. aculeatus*, or *A. nidulans*. Other non-Aspergillus filamentous ascomycete species include Fusarium species, such as *F. graminearum, F. oxysporum, F. solani, F. culmorum* (or corresponding teleomorphs) *Neurospora crassa, Trichoderma reesei, T. viridae, T. harzianum, T. longibranchiatum, Penicillium janthinellum, P. notatum, P. chrysogenum, P. camemberti, P. roqueforti, Humicola insolen, H. grisea* var. *thermoidea, H. lanuginosa, Scytalidium thermophilum, Myceliophthora thermophila*, and *Thielavia terrestris*. The gene, or an oligonucleotide based thereon, can be used as probes in southern hybridization to isolate homologous genes of these other species. In particular, such probes can be used under low to high stringency conditions (for example, prehybridization and hybridization at 42° C. in 5X SSPE, 0.3% SDS, 200 µg/ml sheared and denatured salmon sperm DNA, and either 50, 35 or 25% formamide for high, medium and low stringencies, respectively) for hybridization with the genomic or cDNA of the species of interest, following standard southern blotting procedures, in order to identify and isolate the corresponding cPY gene therein. A PCR reaction using the degenerate probes mentioned herein and genomic DNA or first-strand cDNA from a filamentous fungus may also yield a CPY-specific product which could then be used as a probe to clone the corresponding genomic or cDNA.

The present gene is particularly useful in the creation of carboxypeptidase-deficient mutants of filamentous ascomycetes such as Aspergillus. This can be achieved in a number of ways. In one method, as described in further detail below, a selectable marker is cloned into the middle of the CPY gene. The disrupted fragment is then released from the parental plasmid using restriction enzymes. The linearized DNA fragment is used to transform the chosen host cell. In the host cell, the homologous ends pair with the host cell chromosome, and the homologous recombination results in a chromosomal gene replacement. Useful selectable markers for use with fungal cell hosts include amdS, pyrG, argB, niaD, sC, and hygB. Alternately, a two-step process can be employed using a two-way selectable marker. In such a process, a plasmid containing a truncated CPY gene and the selectable marker gene is digested with a restriction enzyme which cuts once within the the CPY fragment in order to target integration to the CPY locus during transformation. The transformants are then grown on media which will select for the loss of the selectable marker gene, e.g., when the marker is pyrG, the medium may contain 5-fluorootic acid. The loss of the selectable gene usually occurs by a recombination between the wild type CPY and the introduced truncated CPY gene. Approximately 50% of the resulting strain should have only the truncated CPY gene while the other 50% will contain only the wild type gene. Such methods are described in Rothstein, Meth. Enzymol. 194, 281–301, 1991.

The CPY-deficient mutants so created are particularly useful in the expression of heterologous protein. By "heterologous protein" in the present context is meant a protein which is not native to the host cell, a native protein in which modifications have been made to alter the native sequence, or a native protein whose expression is quantitatively altered as a result of a manipulation of the host cell by recombinant DNA techniques. Also encompassed within this term are native proteins for which expression in the mutants involves the use of genetic elements not native to the host cell, or use of native elements which have been manipulated to function in a manner not normally seen in the host cell.

As already noted, the production of proteases by a chosen host cell can severely limit the yield of the desired protein by degrading the product before it can be recovered. The elimination or reduction in the amount of CPY produced by a host can therefore substantially increase the yield of any given protein, and can render an otherwise commercially unsuitable host cell commercially feasible for recombinant protein production. In a preferred embodiment, the CPY deficient cells produce at least 25% less, preferably at least 50% less, and most preferably at least 70% less CPY, up to total loss of CPY function, than the corresponding wild-type strain.

The mutant fungal cells of the present invention can be used in recombinant protein production in the same manner as the wild-type strains. Those skilled in the art will readily recognize routine variations from the specific embodiments described herein which are useful in adapting the methodology to the strains noted above. A gene of interest can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a gene to be used according to the invention is operably linked to the control sequences in the proper reading frame.

The expression vector may be any vector which may conveniently be subjected to recombinant DNA procedures, and the choice of vector will typically depend on the host cell into which it is to be introduced. In a preferred embodiment of the present invention, the host cell is a strain of the genus Aspergillus. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the sequence of the gene of interest should be operably connected to a suitable promoter sequence. The promoter may be any DNA sequence which shows transcriptional activity in the host cell of choice and may be derived from genes encoding proteins either homologous or heterologous to the host cell. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. oryzae* alkaline protease, *A. oryzae* triose phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the heterologous gene sequence. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, or one which confers antibiotic resistance such as ampicillin, kanamycin, chloramphenicol or tetracycline resistance. Examples of Aspergillus selection markers include amdS, pyrG, argB, niaD, sC, and hygB, a marker giving rise to hygromycin resistance. Preferred for use in an Aspergillus host cell are the amdS and pyrG markers of *A. nidulans* or *A. oryzae*. Furthermore, selection may be accomplished by co-transformation, e.g. as described in WO 91/17243.

It is generally preferred that the expression gives rise to a product which is extracellular. The protein of interest may thus comprise a preregion permitting secretion of the expressed protein into the culture medium. If desirable, this preregion may be native to the protein of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from Rhizomucor miehei, the gene for the α-factor from *Saccharomyces cerevisiae* or the calf preprochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis* subtilisin. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The CPY-deficient mutants can be used to express any prokaryotic or eukaryotic protein of interest, and are preferably used to express eukaryotic proteins. Of particular interest for these cells is their use in expression of fungal enzymes such as catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, β-galactosidase, α-glucosidase, β-glucosidase, mannosidase, isomerase, invertase, transferase, ribonuclease, chitinase, and deoxyribonuclease. It will be understood by those skilled in the art that the term "fungal enzymes" includes not only native fungal enzymes, but also those fungal enzymes which have been modified by amino acid substitutions, deletions, additions, or other modifications which may be made to enhance activity, thermostability, pH tolerance and the like. The mutants can also be used to express heterologous proteins of pharmaceutical interest such as hormones, growth factors, receptors, and the like.

The invention will be further illustrated by the following non-limiting examples.

EXAMPLES

ISOLATION OF THE ASPERGILLUS NIGER CPY GENE

A. MATERIALS AND METHODS i. Strains.

The following biological materials are used in the procedures described below. *Escherichia coli* K802 (ek4-(nrca), mcrB, hsdR2, galK2, GalT22, supE44, metB1; *E. coli* SOLR (E14-(mcrA) Δ (mcrCB-hsdSMR-mr') 171, sbcC, recB, recJ, uvrC, umuC::Tn5(kan'), lac, gyrA96, relA1, thi-1, endA1, λ^R[F'prOABlacI^qZΔM15]Su-, *E. coli* JM101supE, thi-1, Δ(lacproAB), [F'traD36, proAB, lacI^qZΔM15], *E. coli* XL-1 Blue recA1, endA1, gyrA96, thi-1, hsdR17, supE44, relA1, lac, [F'proAB, lacI^qZΔM15, Tn10 (tet^R)], *Aspergillus niger* Bo-1, *A. niger* SFAG-2.

ii. PCR amplification.

PCR reactions are run using standard protocols with annealing steps done at 45° C. *A. niger* Bo-1 genomic DNA is used as template and the following degenerate oligonucleotides are used.

| | |
|---|---|
| Primer 1-1 (94-282) | -GGIGGICCIGGITGYTC |
| Primer 1-2 (94-283) | -GGIGGICCIGGITGYAG |
| Primer 2-1 (94-284) | -CCIAGCCARTTRCADAT |
| Primer 2-2 (94-285) | -CCYAACCARTTRCADAT |
| Primer 3-1 (94-331) | -GTIGGITTYTCITAYTCIGG |
| Primer 3-2 (94-332) | -GTIGGITTYAGYTAYAGYGG |
| Primer 4-1 (94-329) | -GARTCITAYGCIGGICAYTA |
| Primer 2-1 (94-330) | -GARAGYTAYGCIGGICAYTA |

In the above primers, I stands for inosine, Y for C or T, R for A or G, and D for A, G or T.

iii. Subcloning PCR products.

PCR products are subcloned for sequencing using the TA Cloning Kit(Invitrogen) following the manufacturer's protocols.

iv. In vivo excision from Lambda Zap II.

From the CPY cDNA Lambda Zap clones, a plasmid is rescued containing the cDNA inserts in a pBluescript SK-vector by passage through the *E. coli* strain SOLR following the protocols provided by Stratagene.

v. DNA sequencing.

Nucleotide sequencing is determined using TAQ polymerase cycle-sequencing with fluorescent labeled nucleotides. The sequencing reactions are electrophoresed on an Applied Biosystems automatic DNA sequencer (Model 363A, version 1.2.0). The following CPY specific primers are used, in addition to the M13 reverse(−48) and M13(−20) forward primers(Sanger et al., J. Mol. Biol. 143: 163–178):

| | |
|---|---|
| 94-376 | TCGCTGCCAGTCTATGATTGA |
| 94-377 | ACATCAACCGCAACTTCCTCT |
| 94-378 | TTGCCAATGAGAACGGACTGC |
| 94-379 | CGCACTTACCACGGACATCAT |
| 94-503 | CAAGCATCCTCAAACTATCGT |
| 94-504 | GAGACGCATGAAGGTGAAGTT |
| 94-505 | GCCGTCCCTCCCTTCCAGCAG |
| 94-506 | GTGCCGACGGGTTCTCCAAGC |
| 94-507 | GCAGCGAGGAAGAGCGTTGTC |
| 94-510 | GGGTCATTCTCGGGGTCATTG |
| 94-511 | GACCCCGAGAATGACCCTGTT |
| 94-512 | GTAGGGCTTCATCCAGTCACC |
| 94-513 | TCTCACCGTTCTCACCAGTAA |
| 94-514 | TCCCTCCCCAAGAAGCACAAC |
| 94-528 | AGCGTCTGGGTTACTGGTGAG |
| 94-529 | AAGATCGGCCAGGTCAAGTCC |
| 94-530 | GAGACGGTGGTAGGGCTTCAT |
| 94-531 | AACGTCGGTTACTCTTACAGC |
| 94-532 | GTGGTCGGGGCGGCGGTTGTG |
| 94-533 | TGTTTGAAGAAGAGGGTAAGC |
| 94-575 | CGCTGCTACTTGATTTTTCTA |
| 94-576 | CTCAGCGCCAACAGCCTCAAT |
| 94-577 | ACCTGCAGTCCGTTCTTATTG |
| 94-634 | TGCGATCGATTCATTCTCATC |
| 94-635 | GGAGTAACCGACATTGACAGG |
| 94-636 | CCTGTCAATGTCGGTTACTCC |
| 94-637 | GTCCCATGGCAACTTCACCTT |
| 94-646 | CTTCTCACCGTTCTCACCAGT |
| 94-647 | CGAGACTCGAAGAACCCTAAG |

B. RESULTS

Using *A. niger* Bo-1 genomic DNA as template PCR reactions are done using various combinations of the CPY specific degenerate oligonucleotides, primers 1-1, 1-2, 2-1, and 2-2 (FIG. 1). All reactions are done using one cycle at 95° C. for 5 minutes, 45° C. for 1 minute and 72° C. for 2 minutes followed by 25 cycles at 95° C. for 1 minute, 45° C. for one minute and 72° C. for 2 minutes. Aliquots (10 μl) of the reactions were electrophoresed on an agarose gel, and in two of the reactions, one with primers 1-2 and 2-1 and one with primers 1-2 and 2-2, an amplification product of approximately 1100 bp is the major species. The predicted size of a product using these oligonucleotide combinations assuming there are no introns within the gene is 900 bp. the 1100 bp amplification product is subcloned and sequenced using the forward and reverse primers. Seven of the subclones are sequenced; however, none of them by homology code for CPY.

PCR reactions using various combinations of primers 3-1, 3-2, 4-1, 4-2, 2-1 and 2-2 are musing the same conditions as above. Aliquots are electrophoresed on an agarose gel, and in two of the reactions, one with primers 4-1 and 2-1 and one with primers 4-2 and 2-1, an amplification product of approximately 600 bp is the major species. The expected size for this amplification product based on homology to other carboxypeptidases is 600 bp. The 600 bp amplification product is subcloned and the DNA sequence is determined for 11 of the subclones using the forward and reverse primers. Nine of the 11 subclones, based on identity of 69% to *S. cerevisiae*, code for CPY from *A. niger*. All 9 are identical to one another suggesting there is only one gene for carboxypeptidase in *A. niger*. The subclone containing the *A. niger* CPY PCR product of 600 bp is designated pDSY17.

A Southern blot of *A. niger* Bo-1 genomic DNA is probed with the insert from DDSY17. The probe is radiolabeled using a nick-translation kit from Gibco-BRL. Hybridization conditions used are 60° C. in 1.5X SSPE, 1% SDS, 0.5% nonfat milk and 200 μg/ml salmon sperm DNA. The blot is washed at 65° C. for 15 minutes twice in 0.2X SSC, 1% SDS and 0.1% Na pyrophosphate. In the BamHI, HindIII and SAII digests, single bands of approximately 10, 5.5 and 7 kb, respectively hybridize to the CPY probe.

In order to isolate the full gene for CPY, a genomic bank in EMBL4 of *A. niger* Bo-1 containing approximately 26,000 recombinants is probed with the PCR-derived CPY gene fragment, radiolabeled with the Gibco-BRL nick translation kit. Approximately 28,000 plaques are lifted to filters and probed. Eleven positives from these plates are picked. After purification, 9 of the primary clones still hybridized with the CPY probe. DNA is isolated from the 9 clones, and restriction digests are done in order to begin characterizing them. From the restriction patterns, 7 of the 9 are identical. The other two clones are unique. From Southern digests of the clones, it is determined that 8 of the 9 have the same HindIII fragment of approximately 5.5 kb which hybridizes to the CPY probe. The clone which does not contain the same HindIII fragment contains a larger (>12 kb) HindIII fragment which hybridizes to the CPY probe. The common HindIII fragment is subcloned for DNA sequencing. The genomic DNK sequence and predicted amino acid sequence is shown in FIG. 1.

A cDNA bank in Lambda ZAPII(Stratagene) of *A. niger* SFAG-2 is also screened. Approximately 42,000 plaques are lifted to filter and probed with the CPY probe as above, and 112 of these plaques appear to hybridize under the stringent conditions defined above. Twenty of the initial positives are picked and rescreened, and upon purification, 18 still hybridize with the CPY probe. From 4 of the positive clones, DNA is isolated using the in vivo excision protocol provided with the Lambda Zap kit. The rescued plasmids are digested with EcoRI and electrophoresed on an agarose gel to determine the sizes of the inserts. Two of the clones (2-1 and 3-2) appear to have large enough inserts to contain the full length cDNA for CPY, and each contains two EcoRI fragments of approximately 1700 and 250 bp. The predicted size for a full length cDNA is approximately 1600 bp. The other two cDNA clones (2-2 and 2-4) have smaller inserts; however, they all contain the 250 bp EcoRI fragment. Partial DNA sequences of clones 3-2 and 2-2 are determined, and 3-2 contains the full-length cDNA while clone 2-2 is truncated at the 5'end by about 200 bp.

The complete cDNA sequence is determined on both strands (FIG. 2). The cDNA is predicted to code for a CPY precursor of 557 amino acids in length. To date most of the nucleotide differences found between the cDNA and genomic clones are within the wobble which is not surprising since they come from two different *A. niger* strains. Based on an alignment with CPY from *S. cerevisiae*, CPY from *A. niger* appears to have both a signal peptide and a propeptide and the mature CPY protein is either 419 or 420 amino acids in length. *A. niger* CPY has approximately 65% and 66% identity to CPY from the yeasts *S. cerevisiae* and *C. albicans* (Mukhtar et al., Gene 121: 173–177, 1992), respectively.

II. PREPARATION OF A CPY-DEFICIENT MUTANT

In order to create an *A. niger* strain deleted for CPY, a construct in which the *A. oryzae* pyrG gene is inserted into the coding region of CPY is made (FIG. 3). An ~6.5 kb HindIII fragment containing almost the entire gene of CPY and ~6 kb downstream of the gene is subcloned into a pKS+(StrataGene) derivative in which the PstI site has been destroyed. The resulting recombinant is digested with PstI to delete an 815 bp fragment from the CPY coding region, and the overhangs created by digestion with PstI are blunted by the addition of T4 DNA polymerase and all 4 dNTPs. The resulting blunt-end vector is ligated to an ~3.8 kb blunt-end fragment obtained by digestion with HindIII followed by a fill-reaction using Klenow fragment. The final construct in which the CPY gene has the pyrG inserted is digested with HindIII to create a linear fragment which is used to transform an *A. niger* pyrG strain selecting for growth on minimal medium plates. Transformants are screened by Southern blotting to determine which strains contain a disrupted CPY gene. The transformants are further analyzed by Western blotting to look for the absence of CPY intracellularly. Once a strain is identified as containing a disruption of CPY, the effect on heterologous protein is determined.

Deposit of Biological Materials

The following biological materials have been deposited on Sep. 13, 1994 in Agricultural Research Service Culture Collection (NRRL) 1815 North University Street, Peoria, Ill. 61664.

| Cell line | Accession No. |
|---|---|
| *E. coli* containing pDSY23 (EMCC #0120) | NRRL B21326 |

What is claimed is:

1. A mutant filamentous ascomycete cell which produces at least 25% less carboxypeptidase Y than a corresponding wild-type cell when cultured under identical conditions, wherein the endogenous carboxypeptidase Y gene has been replaced by homologous recombination with a nucleic acid sequence wherein the nucleic acid sequence is selected from the group consisting of (i) the nucleic acid sequence depicted in SEQ ID NO:1 or SEQ ID NO:3 and (ii) a nucleic acid sequence which hybridizes with SEQ ID NO:1 or SEQ ID NO:3 under high stringency conditions; which sequence has been disrupted; and which cell has been transformed to recombinantly produce a heterologous protein.

2. The cell of claim 1 which produces 50% less carboxypeptidase Y than a corresponding wild-type cell.

3. The cell of claim 1 which produces which produces at least 70% less carboxypeptidase Y than a corresponding wild-type cell.

4. The cell of claim 1, wherein the nucleic acid sequence which has been disrupted is the nucleic acid sequence depicted in SEQ ID NO:1.

5. The cell of claim 1, wherein the nucleic acid sequence which has been disrupted is the nucleic acid sequence depicted in SEQ ID NO:3.

6. The cell of claim 1, wherein the nucleic acid sequence which has been disrupted is a nucleic acid sequence which hybridizes with SEQ ID NO:1 under high stringency conditions.

7. The cell of claim 1, wherein the nucleic acid sequence which has been disrupted is the nucleic acid sequence which hybridizes with SEQ ID NO:3 under high stringency conditions.

8. The cell of claim 1, wherein the nucleic acid sequence has been disrupted by insertion of a selectable marker.

9. The cell of claim 8, wherein the selectable marker is amdS, pyrG, argB, niaD, sC, or hygB.

10. The cell of claim 1 which is selected from the group consisting of Aspergillus, Fusarium, Humicola, Myceliophthora, Penicillium, Thielavia, Trichoderma, and Scytalidium.

11. The cell of claim 10 which is Aspergillus niger.

12. A method for recombinant production of a protein of interest, comprising
(a) culturing the cell of claim 1 under contritions suitable for expression of the protein and;
(b) recovering the protein.

13. The method of claim cell of claim 12 wherein the cell produces at least 50% less carboxypeptidase Y than a corresponding wild-type cell.

14. The method of claim 12 wherein the cell produces at least 70% less carboxypeptidase Y than a corresponding wild-type cell.

15. The method of claim 12 wherein the cell's nucleic acid sequence which has been disrupted is the nucleic acid sequence depicted in SEQ ID NO:1.

16. The method of claim 12 wherein the cell's nucleic acid sequence which has been disrupted is the nucleic acid sequence depicted in SEQ ID NO:3.

17. The method of claim 12 wherein the cell's nucleic acid sequence which has been disrupted is a nucleic acid sequence which hybridizes with SEQ ID NO:1 under high stringency conditions.

18. The method of claim 12 wherein the cell's nucleic acid sequence which has been disrupted is the nucleic acid sequence which hybridizes with SEQ ID NO:3 under high stringency conditions.

19. The method of claim 12 wherein the cell's nucleic acid sequence has been disrupted by insertion of a selectable marker.

20. The method of claim 19, wherein the selectable marker is amdS, pyrG, argB, hinD, sC, or hygB.

21. The method of claim 19 wherein the cell is selected from the group consisting of Aspergillus, Fusarium, Humicola, Myceliophthora, Penicillium, Scytalidium, Thielavia, and Trichoderma.

22. The method of claim 21 wherein the cell is Aspergillus niger.

* * * * *